United States Patent [19]

Heiss et al.

[11] Patent Number: 4,759,713
[45] Date of Patent: Jul. 26, 1988

[54] DISPOSABLE DENTAL TOOL

[75] Inventors: Mark A. Heiss, Chicago; James C. Richardson, Schaumburg; Phillip A. Taylor, Libertyville, all of Ill.

[73] Assignee: Baxter Travenol Laboratories, Inc., Deerfield, Ill.

[21] Appl. No.: 890,258

[22] Filed: Jul. 23, 1986

Related U.S. Application Data

[63] Continuation of Ser. No. 759,023, Jul. 25, 1985, abandoned.

[51] Int. Cl.⁴ ................................................ A61C 3/00
[52] U.S. Cl. ..................................................... 433/141
[58] Field of Search ................ 433/141, 142, 143, 144

[56] References Cited

U.S. PATENT DOCUMENTS

| | | | |
|---|---|---|---|
| 3,775,848 | 12/1973 | Barnett | 433/142 |
| 3,986,264 | 10/1976 | Faierstein | 433/141 |
| 4,060,897 | 12/1977 | Greenstein | 433/141 |
| 4,387,479 | 6/1983 | Kigyos | 432/89 |

Primary Examiner—Robert Peshock
Attorney, Agent, or Firm—Kay H. Pierce; Paul C. Flattery

[57] ABSTRACT

A disposable dental instrument is described in which the instrument is formed by insert molding a handle about a wire. The wire has a working portion and a embedding portion; both the working portion and the embedding portion have a common diameter. In one embodiment of the subject invention, the handle changes color when exposed to ultraviolet light. In another embodiment of the invention, the instrument can be sterilized using only radiation sterilization techniques.

3 Claims, 3 Drawing Sheets

DISPOSABLE DENTAL TOOL

This is a continuation of application Ser. No. 759,023, filed July 25, 1985 and now abandoned.

BACKGROUND OF THE INVENTION

1. Field of the Invention

The invention relates generally to dental tools for removing plaque and more specifically to disposable dental tools for use by a dental professional or a single patient only.

2. Brief Description of the Background of the Invention

Traditionally, dentists have purchased reusable dental tools for removing plaque. Such tools are typically purchased in an unsterilized state and the tools are sterilized prior to use on each patient. If the sterilization process is not performed correctly, the possibility arises that infection may spread from one patient to another. This is particularly undesirable when the form of infection is a herpes, hepatitis, or other presently uncurable virus, such as Acquired Immune Deficiency Syndrome, commonly known as AIDS.

The inventors of the subject invention recognized that one method of preventing infections from being passed from one patient to another is to use disposable dental tools for single-patient use only. However, dental tools currently on the market for professionally removing plaque are relatively expensive and are not amenable to single-patient use.

One relatively inexpensive tool for removing plaque is described in U.S. Pat. No. 4,449,934 to Salam issued May 22, 1984. This tool is intended for nonprofessional use only. The tool is basically a toothbrush with a tapered blade made of a plastic material mounted at the end of the tooth brush. The blade consists of a blunt apex folded about a base-to-apex line and inclined to the axis of the handle to allow outer teeth surfaces as well as spaces in between teeth to be scraped to remove plaque and tartar.

Another dental tool for personal hygiene is described in U.S. Pat. No. 4,326,548 issued Apr. 27, 1982 to Wagner. This tool is a curved metal pick that is embedded in a pen-shaped holder. Again, this tool is designed for nonprofessional use.

Yet another type of dental tool currently available is a heavy scaler manufactured by dvt Dental ab of Sweden which consists of a scaling device having a single curve manufactured from an extruded triangular-shaped metal and embedded in a plastic handle. One of the problems with this device is that since it is manufactured from an extruded triangular-shaped metal; the metal cannot be easily curved. This limits the device to a single-curve device.

SUMMARY OF THE INVENTION

In one embodiment of the invention, a disposable dental instrument for single-patient use is provided which includes a handle. The invention also includes wire means for removing plaque, the wire means being attached to the handle. The wire means includes a working portion for removing plaque and an embedding portion to be embedded in the handle, the wire means has a common diameter for both the working portion and the embedding portion.

In another embodiment of the invention, a disposable dental instrument for single-patient use is provided which includes a handle formed from a material which changes color when exposed to ultraviolet light. The instrument also includes a means for removing plaque attached to the handle.

A method of manufacture of such tools is also provided which includes: forming a wire having a common diameter throughout to provide at least two bends at a first end of the first wire; removing a portion of a first end of the wire of the wire to produce a first plaque-removing edge; and insert molding a material about the wire to create a handle, the first end of the first wire extending beyond the periphery of the handle.

Thus, it is an object of the invention to provide a low-cost dental tool for by a dental profession on a single patient.

It is another object of the invention to provide a low-cost dental tool and method of manufacture thereof in which the tool is for single patient use and the tool is capable of being radiation sterilized.

It is yet another object of the subject invention to provide a dental tool and method of manufacture thereof that is capable of being radiation sterilized, but which degrades upon any attempt to resterilize the tool using heat sterilization techniques.

It is another object of the invention to provide a dental tool and method of manufacture thereof in which the tool changes color when exposed to ultraviolet light.

Still yet another object of the invention is to provide a low-cost presterilized dental tool and method of manufacture thereof for single-patient use.

And still yet another object of the invention is to provide a two-ended dental tool and method of manufacture thereof using single wire construction.

Another object of the invention is to provide a low-cost, two-ended dental tool and method of manufacture thereof using two wire construction.

Another object of the subject invention is to provide a low-cost dental tool and method of manufacture thereof in which a wire is partially embedded in a plastic handle wherein the embedded portion of the wire and the nonembedded portion of the wire have a common diameter.

Other objects, advantages, and novel features of the present invention will become apparent from the following detailed description of the invention when considered in conjunction with the accompanying drawings. Before explaining the embodiments of the invention in detail, it is to be understood that the invention is not limited in its application to the details of the construction and to the arrangement of components as set forth in the following description, or as illustrated in the accompanying drawings. The invention is capable of other embodiments and of being practiced and carried out in various ways. Furthermore, it is to be understood that the phraseology and terminology employed herein are for the purpose of description and should not be regarded as limiting.

DETAILED DESCRIPTION OF THE PREFERRED EMBODIMENT

Figure 1:
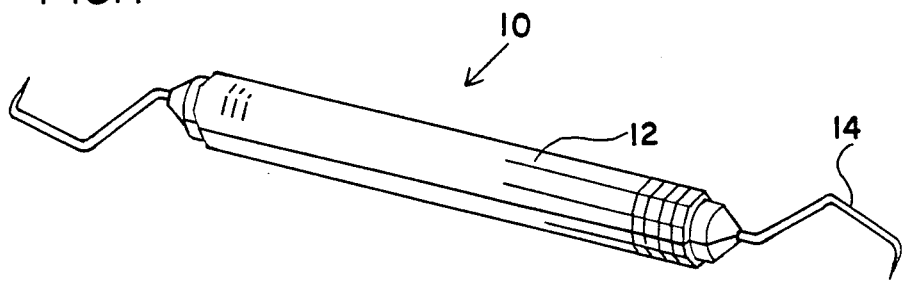
FIG. 1 illustrates one embodiment of the subject invention in which a single wire is embedded in a plastic handle to form a two-ended dental tool.
Figure 2:
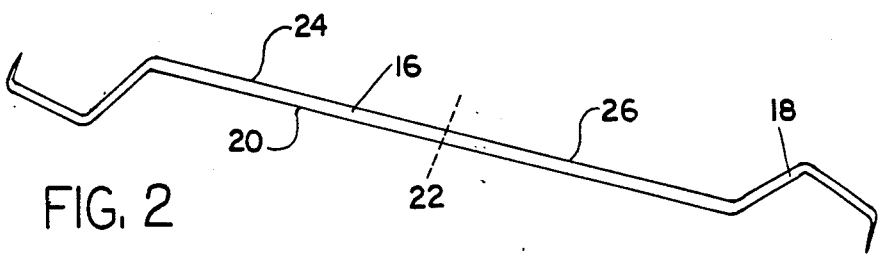
FIG. 2 illustrates the single wire of FIG. 1.

Refer now to FIG. 1 which illustrates a typical disposable dental tool 10 manufactured in accordance with the subject invention. The tool includes a handle 12 and a wire means 14 for removing plaque. The wire means is attached to the handle 12. The wire means 14 is more clearly illustrated in FIG. 2. In the preferred embodiment, the wire means 14 consists of a single wire 16 that includes a working portion 18 for removing plaque and an embedding portion 20 to be embedded into the handle 12. In another embodiment, the single wire 16 may be separated as illustrated in phantom 22, FIG. 2, to form two wire means 24 and 26. In either embodiment, the wire means has a common diameter for both the working portion 18 and the embedding portion 20.

In the preferred embodiment, the handle 12, FIG. 1 is insert molded about the wire means 14. The method of manufacture will be discussed in greater detail below. However, in some embodiments, it is desirable to include a coupling agent in the handle such as methethylketone to enhance bonding between the handle 12 and the embedding portion 20 of the dental tool 10. The handle 10 may be formed of any material which may be injection molded. The choice of material depends on the particular use of the tool 10 and the particular characteristics desired for a specific embodiment, as will be discussed in greater detail below. In general, however, the handle 10 may be formed of a material taken from the group consisting of polyethylene terephthalate, acrylonitrile butadiene styrene, homopolymers and coplymers of ethylene and terephthalate, and polystrene so that the dental tool can be sterilized using standard radiation techniques. It is desirable to be able to provide a low-cost dental tool that is capable of being sterilized using radiation techniques because this technique is considered to be one of the most accurate and fastest techniques for sterilizing vast numbers of components.

In one embodiment of the subject invention, it is desirable to be able to provide dental tools which are capable of being sterilized using radiation techniques, but are incapable of being sterilized using traditional heat sterilization techniques such as steam. This is desirable because most dental offices use heat sterilization techniques. If a dental tool is incapable of being sterilized in a dentist's office, single-patient, as opposed to multiple-patient, use of the tool will be insured. One way of insuring that a dental tool is not resterilized using heat sterilization techniques is to provide a dental tool which will dissolve, distort, melt, change color, disintegrate, or otherwise degrade when the tool is sterilized using heat-sterilization techniques. This can be accomplished to prevent resterilization using steam by providing that the handle of the tool is formed of a material taken from the group consisting of polyethylene terephalate, acrylic, and polystyrene since such materials will degrade when the handle is sterilized using steam-sterilization techniques.

In another embodiment of the subject invention, it is possible to encourage single-patient use of a dental tool by providing a dental tool having a handle which changes color over time when the handle is exposed to ultraviolet light. In this embodiment of the subject invention, the dental tool would be packaged in an opaque package to prevent exposure of the tool to ultraviolet light prior to use. When the tool is taken from the package and used for the first time, it will be exposed to ultraviolet light which will cause it to visibly change colors. This embodiment can be accomplished by providing that the handle is manufactured with an additive added to the materials discussed above taken from the group consisting of photochromic glass silver compound with diathoxy acetopheane, and silver nitrates.

In one embodiment, the additive may be mixed with the material of the handle. In other embodiments, the additive may be coated on the surface of the handle or applied with an adhesive. In other embodiments, it may be desirable to sensitize the material used as the additive so that color changes may occur with lower amounts of additives or in the presence of different regions of the light spectrum. Some materials that can be used as sentizing agents include the class of acetophenones such as 2,2-diethoxye acetophenone, and the class of benzoin ethers such as Vicure-10 TM, a trademark of the Shell Company. In some embodiments, it may be desirable for the handle to be able to change colors in the presence of light in other regions other than the ultraviolet region of the light spectrum. For example, it may be desirable for the handle to change color in the presence of visible light.

Figure 3:
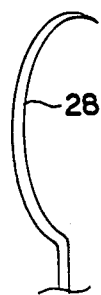
FIGS. 3, 4, and 5 illustrate Gracey curette ends used in accordance with one embodiment of the subject invention.
Figure 4:
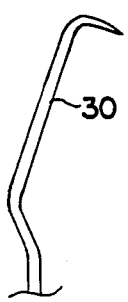
Figure 5:
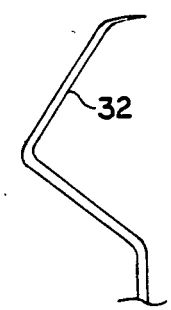
Figure 6:
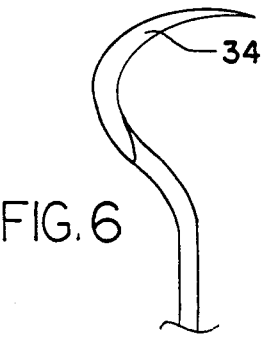
FIGS. 6, and 7 illustrate Jaquette ends used in another embodiment of the subject invention.
Figure 7:
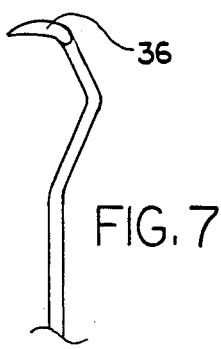

It should be recognized that a wide variety of disposable dental tools for single-patient use can be manufactured using the embodiments described above. FIGS. 3, 4 and 5 illustrate various curette ends 28, 30, and 32, respectively. Similarly, FIGS. 6 and 7 illustrate various jaquette ends 34 and 36, respectively. From the above, it can be seen that numerous other working ends can be provided. However, it is important to note for cost reduction purposes that the working ends provided in accordance with the subject invention differ from traditional working ends in that such ends are formed from a round wire having a diameter which is identical to the diameter of the portion of the wire which is embedded in the handle. This facilitates manufacture of the instruments by conventional wire-forming methods. In the past, dental tools for professional use have had working ends which were hand crafted. The use of a wire having a common diameter throughout in accordance with the subject invention, allows the working end of the tool to be easily formed with multiple bends and machined to produce a scraping edge.

Figure 8:
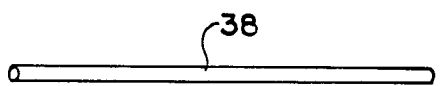
FIGS. 8, 9, 10, 11, and 12 illustrate various manufacturing stages performed when manufacturing dental tools in accordance with the subject invention.

The fabrication steps used in the preferred embodiment are illustrated in greater detail in FIGS. 8 through 12. FIG. 8 illustrates that a conventional wire blank 38 typically made of surgical stainless steel can be used to form the working surface of a dental tool.

Figure 9:
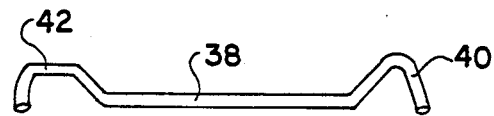

Referring now to FIG. 9 in the preferred embodiment, the wire 38 is formed at both ends 40, 42 to produce a curette, Jaquette, or other style of professional dental instrument. The forming stage is accomplished in the preferred embodiment using a four-station forming press. In other embodiments, other forming devices can be used to bend the wire such as a stamping press.

Figure 10:
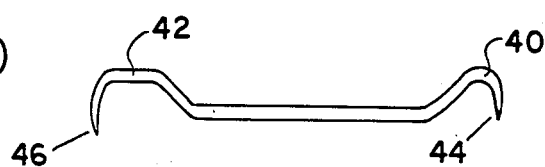

Refer now to FIG. 10 which illustrates that the ends 40, 42 of the wire must be sharpened to form cutting edges 44 and 46. Any type of sharpening technique can be used such as milling, grinding or filing. The shaped wires are then placed in a mold 48, FIG. 12, in the preferred embodiment. The mold is located in a press 50, FIG. 11 where the handles are then overmolded or insert molded on the wires. The working portion of each end of the wire extends beyond the periphery of the handle at opposite ends of the handle in the preferred embodiment. As noted above with respect to FIG. 2, in an alternate embodiment, the wire can be separated so that the final instrument is formed from three pieces rather than two pieces. This may desirable in some embodiments in which custom shapes may be required.

Figure 12:
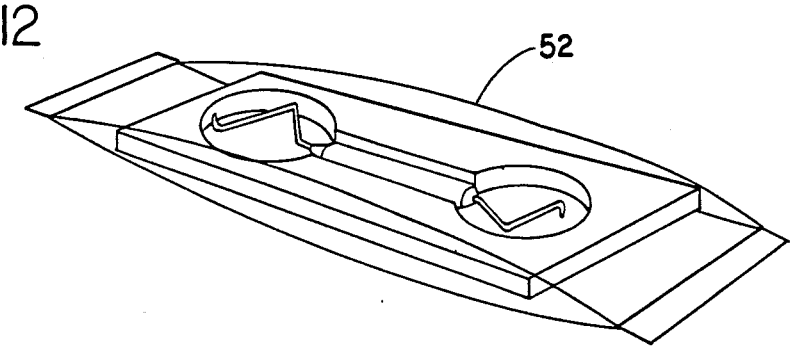
Figure 11:
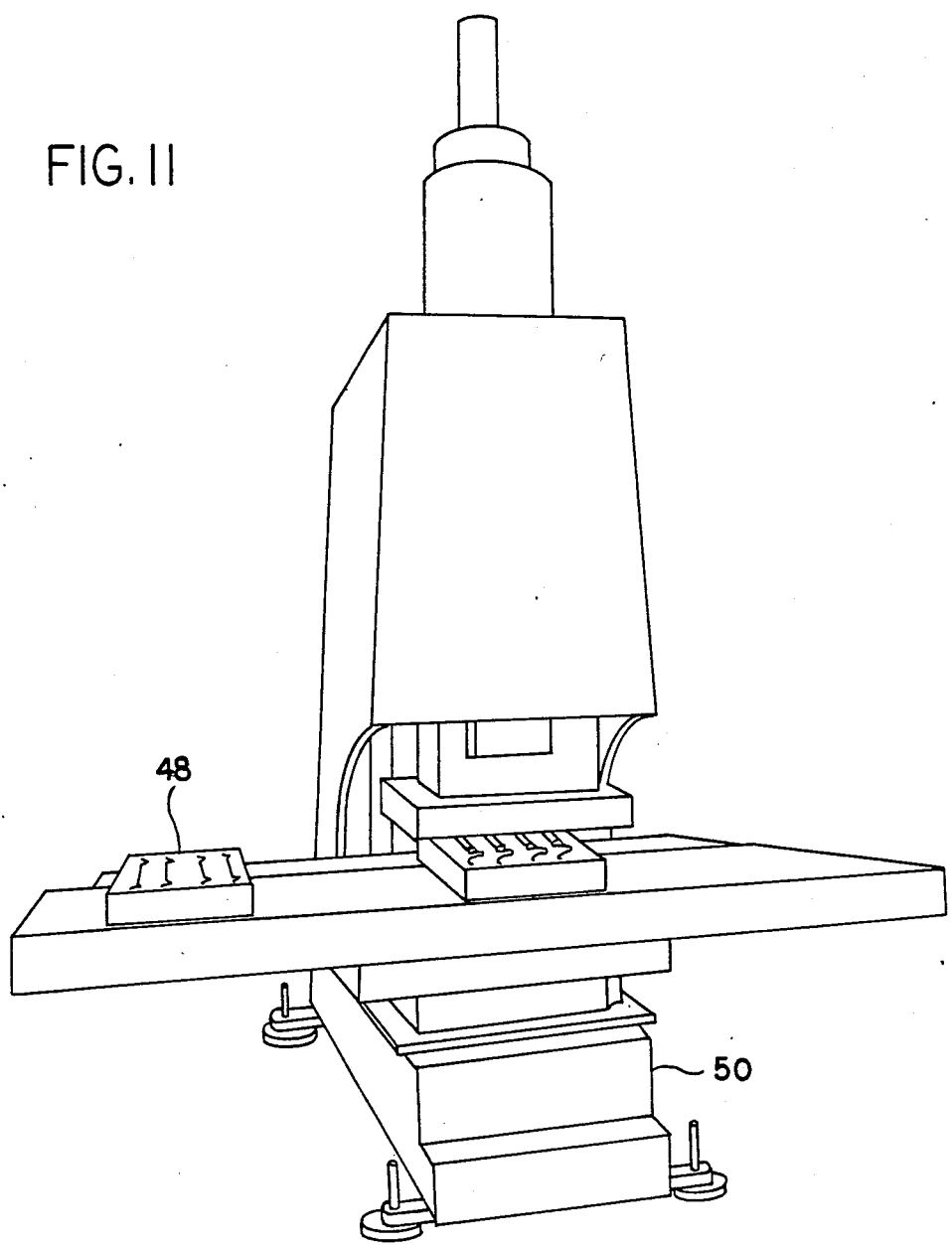

The dental tool may be placed in a package such as a thermo-form package 52 illustrated in FIG. 12. The package and dental tool can then be sterilized using radiation techniques. The instrument is then available for sale to a dentist in a presterilized state.

Thus, as can be seen from the above discussion, the subject invention provides a very low-cost dental tool that is presterilized and is amenable to single-patient use. Such tools are highly desirable to prevent the spread of infectious diseases. Such tools are also desirable for veterinary applications due to the need for low-cost tools.

The fact that the tools can be manufactured so that they will degrade when exposed to heat-sterilization techniques presents an advance over the art because this capability encourages single-patient use of a tool. Embodiments of the subject invention in which the handle of the dental tool changes color when exposed to ultraviolet light also represents an advance over the art because this allows a dentist or other professional practitioner to be immediately aware that a tool is no longer sterile. This characteristic provides valuable protection to a patient.

Although the invention has been described and illustrated in detail, it is to be clearly understood that the same is by way of illustration and example only, and is not to be taken by way of limitation; the spirit and scope of this invention being limited only by the terms of the appended claims.

That which is claimed:

1. A disposable dental instrument for single-patient use comprising:
   a handle formed principally of a material taken from the group consisting of polyethylene; polystyrene; copolymers of acrylonitrile, butadiene, and styrene; homopolymers and copolymers of ethylene terephthalate so that said dental instrument can be sterilized using radiation and ethylene oxide techniques so that said handle will degrade when said handle is sterilized using heat sterilization techniques;
   wire means for removing plaque attached to said handle, said means including a working portion for removing plaque and an embedding portion to be embedded in said handle.

2. A disposable dental instrument for single-patient use comprising:
   a handle formed principally of polyethylene terephthalate so that said handle will degrade when said handle is sterilized using heat sterilization techniques, but can be sterilized using radiation techniques; and
   wire means for removing plaque attached to said handle, said means including a working portion for removing plaque, and an embedding portion to be embedded in said handle.

3. A disposable dental instrument for single-patient use comprising:
   wire means for removing plaque, including a working portion and an embedding portion;
   handle means for embedding said embedded portion of said wire means, said handle means being formed principally of a material that will degrade when said handle means is sterilized using heat sterilization techniques, but will not degrade when said handle is sterilized using radiation techniques.

* * * * *